United States Patent [19]

Cavaterra et al.

[11] Patent Number: 4,871,707

[45] Date of Patent: Oct. 3, 1989

[54] METHOD FOR PREPARING A CATALYST FOR THE SYNTHESIS OF 1,2-DICHLOROETHANE

[75] Inventors: Enrico Cavaterra, Saronno; Alessandro Bossi, Novara, both of Italy

[73] Assignee: Ausimont S.p.A., Milan, Italy

[21] Appl. No.: 940,204

[22] Filed: Dec. 15, 1986

Related U.S. Application Data

[63] Continuation of Ser. No. 777,341, Sep. 18, 1985, abandoned.

[30] Foreign Application Priority Data

Sep. 19, 1984 [IT] Italy ................................ 22717 A/84

[51] Int. Cl.$^4$ ...................... B01J 21/04; B01J 27/122; B01J 27/138
[52] U.S. Cl. ..................................... 502/225; 502/341
[58] Field of Search ....................... 502/225, 341, 346; 570/245

[56] References Cited

U.S. PATENT DOCUMENTS 4,124,534 11/1978 Leitert et al. ........................ 502/225
4,323,716 4/1982 Canavesi et al. ................ 570/245 X
4,587,230 5/1986 Cavaterra et al. ................... 502/225

FOREIGN PATENT DOCUMENTS 971996 10/1964 United Kingdom ................ 570/245

OTHER PUBLICATIONS

Above references were cited in applicants' Ser. Nos. 591,993 and 742,238.

*Primary Examiner*—W. J. Shine
*Attorney, Agent, or Firm*—Stevens, Davis, Miller & Mosher

[57] ABSTRACT

A method for preparing a catalyst for the synthesis of 1,2-dichloroethane by oxychlorination of $C_2H_4$ within a fluidized bed, said catalyst containing magnesium, from 1 to 10% by weight of Cu and a carrier consisting of $Al_2O_3$, said carrier being impregnated, with an aqueous solution containing both $CuCl_2$ and $MgCl_2$, the amount of $MgCl_2$ being such that the molar ratio:

$$X = \frac{\text{Al on the surface}}{\text{Cu on the surface}}$$

as defined in the text, is at least 40% higher than the molar ratio:

$$Y = \frac{\text{Total Al present within the catalyst}}{\text{Total Cu present within the catalyst}}$$

the ratio $W = X:Y$ being therefore $\geq 1.40$ and the surface area of the carrier ranging between 80 and 170 sq.m/g.

5 Claims, No Drawings

METHOD FOR PREPARING A CATALYST FOR THE SYNTHESIS OF 1,2-DICHLOROETHANE

This application is a continuation of application Ser. No. 777,341, filed 9/18/85, now abandoned.

This invention relates to a method for preparing a catalyst for the synthesis of 1,2-dichloroethane by oxychlorination of $C_2H_4$ within a fluidized bed, said catalyst containing from 1 to 10% by weight of Cu and moreover Mg, as well as a carrier consisting of $Al_2O_3$.

BACKGROUND OF THE INVENTION

Catalysts of the aforesaid type have been described, as well as the respective methods of preparing them, in several patents. See, for instance, British Pat. No. 971,996, U.S. Pat. No. 4,124,534, British Pat. No. 1,345,653 and the pending application of Enrico Cavaterra et al Ser. No. 742,238 filed June 7, 1985 (now U.S. Pat. No. 4,587,230) which disclose the impregnation of alumina with solutions of $CuCl_2$ and $MgCl_2$.

In the first cases, however, i.e., British Pat. Nos. 971,996 and 1,345,653 and U.S. Pat. No. 4,124,534, no precise direction is given sufficient to obtain the high yields required by modern plants and, at the same time, a satisfactory degree of fluidization.

These results, on the contrary, can be obtained by using the catalyst according to the aforesaid Cavaterra et al application. Also in this case, however, there are drawbacks; in fact, said application teaches that excellent performances can be achieved only if the catalyst is treated with aqueous hydrochloric acid (HCl), which may involve some problems concerning the ecology and corrosion in the plant, during the catalyst preparation.

THE PRESENT INVENTION

We have now surprisingly found that the same excellent performances as are achieved according to the Cavaterra et al application can be achieved without using HCl during preparation of the catalyst, provided $CuCl_2$ and $MgCl_2$ are added at the same time and provided the surface area of the carrier ranges between 80 and 170 sq.m/g. In other words, we have discovered that, when the surface area of the carrier has a value in the stated range, (and should the amount of magnesium chloride be sufficiently high), the magnesium chloride acts as regulator of the copper on the surface, a function which had been ascribed to HCl.

In broad terms, the molar ratio Mg/Cu in the impregnating solution must be in the range between 0.4 and 1.2 and in any case such that the molar ratio:

$$X = \frac{\text{Al on the surface}}{\text{Cu on the surface}}$$

as defined hereinafter, is at least 40% higher than the molar ratio:

$$Y = \frac{\text{total Al present within the catalyst}}{\text{total Cu present within the catalyst}}$$

that is to say: $W = X/Y \geq 1.40$.

According to a presently preferred embodiment of the invention:
the catalyst contains from 3 to 6% by weight of copper;
said X ratio is equal to or higher than 40:1;
the amount of magnesium in the catalyst (and in the solution) ranges between 0.5 and 1.1 moles per mole of copper.

Said molar ratio:

$$X = \frac{\text{Al on the surface}}{\text{Cu on the surface}}$$

must be determined according to the technique known as XPS analysis (described hereinafter), that supplies the data pertinent to a superficial micro-layer having a thickness ranging between 2 and 3 nm (20–30 Å). Generally, according to the method of the invention, the copper concentration on the surface has to be nil or, in any even, much lower than the copper concentration within the layers directly underlying the superficial layer, said superficial layer having substantially a thickness from 2 to 3 nm.

The catalysts according to the invention display excellent fluidization features and maintain high HCl conversions, also in the case of high $HCl/C_2H_4$ ratios, so that high dichloroethane (DCE) yields with respect to $C_2H_4$ are achieved.

In the catalysts according to the invention, considering the single granule, the Cu lies prevailingly inside the pores, namely is laid on the inner surface of same; such share of Cu, although concerned in the conversion cycles and in the equilibria among the various forms ($Cu_2Cl_2$, $Cu_2Cl_4$, etc.), depending on the $HCl/C_2H_4$ feed ratio, does not give place to the sticking phenomenon, that, on the contrary, involves the zones of possible contact among the different granules.

The outstanding feature of the present catalysts is that, in practice, the active part is almost completely segregated inside the pores of the carrier, the Cu concentration on the outer surface being very slight and at any rate, clearly lower than the Cu concentration on the outer surface which is a disadvantage of the conventional catalysts, as shown by measurements carried out by means of the XPS technique and, furthermore, it remains the same after long periods of time.

By using these catalysts, the reaction within a fluidized bed can be carried out without any adverse effect on the fluidization, using high $HCl/C_2H_4$ ratios in the feed and with high HCl conversions, so that high yields of DCE are obtained with respect to ethylene. The conditions of use of these catalysts do not substantially differ from those of the catalysts previously described in the art. $C_2H_4$, HCl and a gas containing $O_2$ (generally air) are fed in a gaseous phase, Pre-heated up to a temperature close to, but not higher than, the reaction temperature, the latter ranging between 200° and 250° C., preferably between 220° and 235° C. The other operating parameters are generally comprised within the following ranges:

(A) Air/ethylene ratio: it must be such that the $O_2$ content, in the gaseous exhausts, after condensation of DCE, $H_2O$ and HCl, ranges between 3 and 10% by volume.

(B) HCl/ethylene ratio: it must be the closest possible to the stoichiometric value (2/1 molar) compatible with the maintenance of good fluidization conditions of the catalytic bed and of a sufficiently high conversion of HCl, conditions which depend, as already noted, on the specific catalyst.

(C) Contact time (expressed as a ratio between the volume of the catalytic bed in a fluidized state and the volumetric flow of the reactant mixture, under the temperature and pressure conditions existing in the catalytic bed): it depends essentially on the specific type of catalyst; generally it ranges between 10 and 40 seconds, preferably between 20 and 30 seconds.

(D) Linear velocity of the gases (expressed in cm/s): it is chosen within the range between the rate of a minimum fluidization and the entrainment rate, both being typical for the type of catalyst; generally said rate ranges between 10 and 50 cm/s, preferably between 20 and 40 cm/s.

(E) Total pressure during the reaction (important for achieving an effective contact among the reactants, in a gaseous phase, and the catalyst, in a solid phase): generally pressures are used higher than the atmospheric pressure, up to 6 bar; at higher pressures energy waste becomes predominant, due to the compression work.

The following examples are given for purely illustrative and not limiting purposes.

OPERATING CONDITIONS COMMON TO THE DIFFERENT EXAMPLES

The measurement of the outer surface concentration of Cu was carried out by means of the XPS technique (see C. D. Wagner: Handbook of X-Ray Photoemission Spectroscopy; Perkin Elmer Co., Eden Prairie; 1979) based on X-ray irradiation and on the measurement of the energy level and of the energy intensity of the electrons emitted by the solid. The energy level of such electrons is characteristic of the element and the energy intensity is proportional to the number of atoms present in the volume of sample, down to a depth substantially from 2 to 3 nm (20–30 Å) from the surface. As the average size of the catalysts lies around 50 micrometers (in literature values from 20 to 80 nm are usually cited) the measure of the atomic concentrations refers to about 1 ten-thousandth of the granule diameter, namely, essentially to its outer surface. In detail, a small amount of a sample (a few mg) was pressed onto a small plate of pure indium in order to obtain an analyzable surface having an area equal to a few sq. nm; the samples were then analyzed under a high-pushed vacuum at a basic pressure of $2.10^7$ Pa, using an X-ray source working at 400 W and fitted with a Mg anode (K $\alpha$ radiation of magnesium). The photoemission spectra of the present elements, that is 0/1s, C1/2p, Mg/2p, Al/2p, were gathered under conditions of high resolution with the help of a computer for the digitalized acquisition of the data, with a maximation of the signal/noise ratio. After removal of the background noise, the areas of the photoemission peaks were calculated by means of numerical integration; the intensity value thus obtained, corrected for the respective sensitivity factor, was directly proportional to the surface atomic concentration of the respective element.

All catalyst was prepared by means of the "dry impregnation" technique, described for instance by A. V. Neimark, L. I. Kheifex and V. B. Fenelonov on Ind. Eng. Chem. Prod. Res. Dev. 1981, 20, page 441.

EXAMPLE 1

(Preparation of the Catalyst by Means of a "Dry Impregnation")

A miscrospheroidal alumina having a surface area of 170 sq. m/g and an average particle diameter of 50 micrometers was chosen as carrier and the volume of the impregnating solution was equal to the volume of the alumina pores; said solution contained:

$CuCl_2$, in an amount such that the final catalyst contained 4.16% by weight of Cu;

0.736 moles of $MgCl_2$ per mole of Cu.

More in detail, the operating conditions described hereinafter were followed:

(A) 10.5 l of deionized water were heated to 0° C. and 6.083 kg of $CuCl_2.2H_2O$; 5,291 kg of $MgCl_2. 6H_2O$ were then added, under stirring. Heating and stirring were carried on until a complete dissolution was achieved and the solution thus obtained was then cooled down to 25° C.;

(B) 43.0 kg of said alumina were put into a rotary container and the solution obtained according to (A) was slowly sprayed, in a period of time of 1 hour, onto the alumina, kept under stirring by the rotation of the container, taking care to avoid the formation of clots. Afterwards, the temperature was raised up to 150° C., with a gradient of 25° C./h and said temperature was kept at 150° C. for a further 3 hours. The catalyst was then cooled down slowly to 40° C., keeping the container under constant rotation. The analysis gave the results shown in Table 1.

EXAMPLES 2, 3, 4

(Behaviour of the Catalyst)

The catalyst of Example 1 was introduced into a glass reactor having a diameter of 4 cm and a height of 3 m, suited for withstanding pressures up to 6 bar, said catalyst was then activated in situ at 180° C. for 4 hours in the air. The thus activated catalyst was tested in an oxychlorination of $C_2H_4$ within a fludized bed at a pressure of 4 bar (absolute), according to a molar ratio air/$C_2H_4$ equal to 3.2 and with a contact time of 28 seconds; data and results are shown in Table 2.

EXAMPLE 5

(Comparative)

Example 1 was repeated but omitting completely the addition of Mg; the results of Table 1 were obtained.

EXAMPLES 6 and 7

(Comparative)

Examples 2 and 3 were repeated, but the catalyst was replaced by the product lacking in magnesium, prepared according to Example 5. Data and results are shown in Table 2. All these examples show that the lower concentrations of Cu on the surface (corresponding to higher Al/Cu ratios) lead to better fluidization characteristics of the catalyst, which allows to work with higher HCl/$C_2H_4$ feed ratios and thus to obtain higher yields in dichloroethane.

TABLE 1

| Examples | % of atoms on the surface | | | $X = \frac{\text{Al on the surface}}{\text{Cu on the surface}}$ | $Y = \frac{\text{Total Al}}{\text{Total Cu}}$ | $W = \frac{X}{Y}$ |
| | Cu | Cl | Al | | | |
| --- | --- | --- | --- | --- | --- | --- |
| 1 | 2.1 | 7.7 | 90.2 | 42.9 | 25.3 | 1.69 |

TABLE 1-continued

| Examples | % of atoms on the surface Cu | Cl | Al | $X = \dfrac{\text{Al on the surface}}{\text{Cu on the surface}}$ | $Y = \dfrac{\text{Total Al}}{\text{Total Cu}}$ | $W = \dfrac{X}{Y}$ |
|---|---|---|---|---|---|---|
| 5 (*) | 3.7 | 7.7 | 88.6 | 24.1 | 26.7 | 0.90 |

(*) Comparative.

TABLE 2

| Examples | $\dfrac{\text{Al}}{\text{Cu}}$ | Activation T (°C.) | Oxychlorination T (°C.) | HCl/C$_2$H$_4$ (by moles) | DCE yield (molar % on fed C$_2$H$_4$) | HCl Conversion (%) | Fluidization |
|---|---|---|---|---|---|---|---|
| 2 | 42 | 180 | 225 | 1.824 | 91.1 | 99.9 | Excellent |
| 3 | 42 | 180 | 225 | 1.946 | 96.6 | 99.3 | Excellent |
| 4 | 42 | 180 | 225 | 1.990 | 97.7 | 98.2 | Excellent |
| 6 | 24.1 | 180 | 225 | 1.816 | 90.7 | 99.9 | Good |
| 7 | 24.1 | 180 | 225 | 1.926 | 95.7 | 99.4 | Bad |

What is claimed is:

1. A method for preparing a catalyst for the synthesis of 1,2-dichloroethane by oxychlorination of $C_2H_4$ within a fluidized bed, said catalyst containing from 1 to 10% by weight of Cu, from 0.4 to 1.2 moles of magnesium per mole of Cu, and a carrier consisting of microspheroidal $Al_2O_3$, said carrier having a surface area ranging from 80 to 170 m$^2$/g, and said method being characterized in that the carrier is impregnated with an aqueous solution containing both $CuCl_2$ and $MgCl_2$, but without using aqueous HCl during preparation of the catalyst, according to the dry impregnation technique, whereby the molar ratio:

$$X = \frac{\text{Al on the surface}}{\text{Cu on the surface}}$$

as defined in the specification, is at least 40% higher than the molar ratio:

$$Y = \frac{\text{Total Al present within the catalyst}}{\text{Total Cu present within the catalyst}}$$

the ratio $W = X:Y$ being therefore $\geq 1.40$, after which the catalyst is dried and activated.

2. The method of claim 1, wherein said catalyst contains from 3 to 6% by weight of Cu.

3. The method of claim 1, wherein the ratio X is equal to or higher than 40.

4. The method of claim 1, wherein the amount of magnesium in the catalyst is from 0.5 to 1:1 moles per mole of copper.

5. A catalyst obtained by the method of claim 1, wherein the copper concentration on the outer surface of the carrier is nil or at least in a ratio not higher than 1:1.40 with respect to the average copper concentration in the layers underlying the superficial layer, said superficial layer having substantially a thickness of 2 to 3 nm.

* * * * *